United States Patent [19]
Lescallett et al.

[11] Patent Number: 6,051,379
[45] Date of Patent: *Apr. 18, 2000

[54] CANCER SUSCEPTIBILITY MUTATIONS OF BRCA2

[75] Inventors: Jennifer Lee Lescallett, Great Falls, Va.; Tammy Lawrence, Laurel; Antonette Preisinger Allen, Severn, both of Md.; Sheri Jon Olson, Falls Church, Va.; Denise Bernadette Thurber, Silver Spring; Marga Belle White, Frederick, both of Md.

[73] Assignee: Oncormed, Inc., Gaithersburg, Md.

[*] Notice: This patent issued on a continued prosecution application filed under 37 CFR 1.53(d), and is subject to the twenty year patent term provisions of 35 U.S.C. 154(a)(2).

[21] Appl. No.: 08/984,034

[22] Filed: Dec. 2, 1997

Related U.S. Application Data

[60] Provisional application No. 60/059,595, Sep. 23, 1997.
[51] Int. Cl.⁷ .............................. C12Q 1/68; C07H 21/04
[52] U.S. Cl. .................... 435/6; 536/24.31; 536/24.33
[58] Field of Search ........................ 536/24.33, 24.31, 536/24.5; 435/6, 91.2, 320.1

[56] References Cited

U.S. PATENT DOCUMENTS 4,683,195  7/1987  Mullis et al. ............................ 435/6

OTHER PUBLICATIONS

Panayiotiais P., et al. British Journal of Haematology 97:844–847 (1997).

Tavitigian et al. Nature Genetics 12: 333–337 (1996).

*Primary Examiner*—Lisa B. Arthur
*Attorney, Agent, or Firm*—Baker Botts

[57] ABSTRACT

New mutations have been found in the BRCA2 gene. The mutations are located at nucleotide numbers 2192, 3772, 5193, 5374, 6495 or 6909 of the published nucleotide sequence of BRCA2 gene. A process for identifying a sequence variation in a BRCA2 polynucleotide sequence is disclosed. The identification process includes allele specific sequence-based assays of known sequence variations. The methods can be used for efficient, and accurate detection of a mutation in a test BRCA2 gene sample.

44 Claims, No Drawings

CANCER SUSCEPTIBILITY MUTATIONS OF BRCA2

This application is in part based on provisional patent application 60/059,595 filed Sep. 23, 1997, the contents are incorporated by reference.

FIELD OF THE INVENTION

This invention relates to the breast cancer succeptibility gene BRCA2. More specifically, this invention detects germline mutations of the BRCA2 gene that are associated with a predisposition to breast, ovarian and associated cancers. Methods and reagents for detecting the presence of these mutations are included.

BACKGROUND OF THE INVENTION

BRCA2, located on chromosome 13q12-q13, consists of over 70 kb of genomic DNA. The coding sequence produces a protein of 3,418 amino acids. Although most of the exons are small, exons 10 and 11 represent approximately 60% of the entire coding region. BRCA2 is thought to be a tumor suppressor gene associated with breast and ovarian cancer. Thus mutations which form an altered tumor suppressor or altered concentrations of tumor suppressor may be indicative of a higher susceptibility to certain cancers.

The nucleotide sequence for at least one BRCA2 gene is known and is reported in GENBANK accession Number U43746. The BRCA2 gene sequence is available on the Breast Cancer Information Core.

Germline mutations of BRCA2 are predicted to account for approximately 35% of families with multiple case, early onset female breast cancer, and they are also associated with an increased risk of male breast cancer, ovarian cancer, prostrate cancer and pancreatic cancer.

The location of one or more mutations of the BRCA2 gene provides a promising approach to reducing the high incidence and mortality associated with breast and ovarian cancer through the early detection of women at high risk. These women, once identified, can be targeted for more aggressive prevention programs. Screening is carried out by a variety of methods which include karyotyping, probe binding and DNA sequencing. In such cases where one or only a few known mutations are responsible for the disease, such as testing family members, methods for detecting the mutations are targeted to the site within the gene at which they are known to occur.

Many mutations and normal polymorphisms have already been reported in the BRCA2 gene. A world wide web site has been built to facilitate the detection and characterization of alterations in breast cancer susceptibility genes. Such mutations in BRCA2 can be accessed through the Breast Cancer Information Core at:
HTTP://www.nchgr.nih.gov/dir/lab_transfer/bic.

While mutations occur throughtout the BRCA2 gene, there is a need for a high sample number (throughput), sensitivity, accuracy and cost effectiveness. Identification of mutations of the BRCA2 gene would allow more widespread diagnostic screening for hereditary breast and ovarian cancer than is currently possible and permit identification of functional areas deduced from the mutational spectrum observed.

SUMMARY OF THE INVENTION

The present invention is based on the discovery of six mutations in the BRCA2 gene sequence which is associated with susceptibility to and development of breast and ovarian cancer. Specifically, mutations located at nucleotide numbers 2192, 3772, 5193, 5374, 6495 and 6909 have been discovered.

It is an object of the invention to provide a method for determining a predisposition or higher susceptibility to breast, ovarian and other cancers.

It is another object of the invention to provide primers for detecting and amplifying a region of DNA which contains the BRAC2 mutations.

It is another object of the invention to provide probes for detecting a region of DNA which contains the BRAC2 mutations.

It is a further object of the invention to provide a method of characterizing and classifying a tumor and determining a therapy dependant upon the type of mutation(s) present.

It is also an object of the present invention to provide a mutant BRCA2 gene and expressed mutant protein for drug development, gene therapy and other uses to prevent or amelorate the effects of or resulting from the mutant BRCA2 gene.

DETAILED DESCRIPTION OF THE PREFERRED EMBODIMENTS

For defining the present invention, the following nomenclature is used to describe the mutation due to an inconsistency in the published literature. Beaudet et al, *Human Mutations*, 2: 245–248 (1993), Antonarakis et al, *Human Mutations*, 4: 166 (1994), Cotton, *Human Mutations*, 8: 197–202 (1996), and Beutler et al, *Human Mutations*, 8: 203–206 (1996). In defining the mutation, the number indicates the nucleotide number corresponding to the BRCA2 gene sequence where the mutation first occurs. Other BRCA2 sequences (haplotypes) which are polymorphisms or genetic variations of BRCA2 may used, in which a corresponding mutation at the corresponding nucleotide number are present. Different sequence variations in a normal BRCA1 gene have been discovered previously by the inventors (U.S. Pat. No. 5,654,155) and sequence variations in a normal BRCA2 gene sequence are expected. Also note Shattuck-Eidens, et al, *Journal of the American Medical Association*, 278: p. 1242 (1997). Generally, the sense strand is referred to. For simplified identification purposes of this application, reference is to the BRCA2 sequence referenced above, however the invention is equally applicable to all of the normal BRCA2 sequences.

Insertion mutations are indicated by "ins" and deletion mutations are indicated by "del". The letters after "ins" or "del" refer to the nucleotide(s) which were inserted or deleted. Insertions and deletions above two nucleotides are indicated by the number of nucleotides inserted or deleted. When the mutation results in one nucleotide being substituted for another, the nucleotide of the BRCA2 gene sequence is placed to the left of the number and the nucleotide found in the mutation is placed to the right of the number.

The first mutation is referred to as C2192G. This mutation or genetic alteration causes a change in nucleotide number 2192 from C to G resulting in codon 655 being changed from proline to arginine. Any amino acid change can have a dramatic change in biological activity. Some people believe that since proline can form a turn in the chain of amino acids in the protein, the removal of this turn, particularly when substituted with a charged amino acid may change the three dimentional configuration of the protein or at least may negatively affect on the biological activity of the resulting protein.

The second mutation is referred to as 3772delTT. This mutation deletes TT at nucleotide number 3772 causing a frameshift mutation and forming an in-frame stop codon at codon 1182. It has been demonstrated that a truncated, and most likely non-functional, protein has been produced by this mutation.

The third mutation is referred to as C5193G. This mutation substitutes G for C at nucleotide number 5193 causing a stop codon (TAG) to be formed at codon 1655. It has been demonstrated that a truncated, and most likely non-functional, protein has been produced by this mutation.

The fourth mutation is referred to as 5374del4. This mutation deletes TATG at nucleotide number 5374 causing a frameshift mutation and forming an in-frame stop at codon 1723. It has been demonstrated that a truncated, and most likely non-functional, protein has been produced by this mutation.

The fifth mutation is referred to as 6495delGC. This mutation deletes GC at nucleotide number 6495 causing a frameshift mutation and forming an in-frame stop codon at codon 2090. It has been demonstrated that a truncated, and most likely non-functional, protein has been produced by this mutation.

The sixth mutation is referred to as 6909insG. This mutation inserts a G at nucleotide number 6909 causing a frameshift mutation and forming an in-frame stop codon at codon 2232. It has been demonstrated that a truncated, and most likely non-functional, protein has been produced by this mutation.

The presence of truncated proteins was demonstrated by expression of overlapping portions of the mutant genes and measuring molecular weight by gel electrophoresis.

Useful DNA molecules according to the present invention are those which will specifically hybridize to BRCA2 sequences in the region of the C2192G, 3772delTT, C5193G, 5374del4, 6495delGC or 6909insG mutations. Typically these DNA molecules are 17 to 20 nucleotides in length (longer for large insertions) and have the nucleotide sequence corresponding to the region of the mutations at their respective nucleotide locations on the BRCA2 gene sequence. Such molecules can be labeled, according to any technique known in the art, such as with radiolabels, fluorescent labels, enzymatic labels, sequence tags, biotin, other ligands, etc.

According to another aspect of the invention, the DNA molecules, or oligonucleotides, contain one or more of the specific mutations. Generally it is preferred for each DNA probe to encompass only one mutation. Such molecules may be labeled and can be used as allele-specific oligonucleotide probes to detect the mutation of interest.

Polynucleotide containing biological samples, such as blood, can be tested to determine whether the BRCA2 gene contains one of the specific mutations listed above. To amplify the BRCA2 gene, one may use polymerase chain reaction (PCR) using primers which hybridize to the ends of the exons or to the introns flanking the exons. In the situation of exon 11, the exon is so large that using plural pairs of primers to amplify overlapping regions is preferred. Such was actually used in the Examples below.

Amplification may also be performed by a number of other techniques such as by cloning the gene and linking the BRCA2 gene or fragments thereof in the sample to a vector. "Shot gun" cloning is particularly preferred. For the purposes of this application, a vector may be any polynucleotide containing system which induces replication such as a plasmid, cosmid, virus, transposon, or portions thereof.

In one embodiment of the invention a pair of isolated oligonucleotide primers are provided.
BRCA2-11F 5'TGG TAC TTT AAT TTT GTC ACT T3' SEQ ID NO:1
BRCA2-11R 5'TGC AGG CAT GAC AGA GAA T3' SEQ ID NO:2
The designation BRCA2-11 refers to a sequence in or near exon 11 of the BRCA2 gene. F and R refer to forward and reverse.

The oligonucleotide primers are useful in directing amplification of a target polynucleotide prior to sequencing. These unique BRCA2 exon 11 oligonucleotide primers were used to scan the BRCA2 gene to find the mutations. From the sequence information, the probes were designed and produced to assay for the mutation based upon identification of the C2192G mutation.

In another embodiment of the invention a pair of isolated allele specific oligonucleotide probes are provided.
5'TGA AGA ACC AAC TTT GT3' SEQ ID NO:3
5'TGA AGA ACG AAC TTT GT3' SEQ ID NO:4
These allele specific oligonucleotides are useful in diagnosis of a subject at risk of having breast or ovarian cancer. The allele specific oligonucleotides hybridize with a target polynucleotide sequence containing the C2192G mutation. 5'TGA AGA ACC AAC TTT GT3', SEQ ID NO:3, hybridizes preferentially to the wildtype sequence and is useful as a control sequence. 5'TGA AGA ACG AAC TTT GT3', SEQ ID NO:4, is designed to hybridize preferentially to the mutant sequence.

In a second embodiment of the invention a pair of isolated oligonucleotide primers are provided.
BRCA2-11F 5'CTC AGA TGT TAT TTT CCA AGC3' SEQ ID NO:5
BRCA2-11R 5'CTG TTA AAT AAC CAG AAG CAC3' SEQ ID NO:6
The oligonucleotide primers are useful in directing amplification of a target polynucleotide prior to sequencing. These unique BRCA2 exon 11 oligonucleotide primers were used to scan the BRCA2 gene to find the mutations. From the sequence information, the probes were designed and produced to assay for the mutation based upon identification of the 3772delTT mutation.

In another embodiment of the invention a pair of isolated allele specific oligonucleotides are provided.
5'GCA AGC AAT TTG AAG GT3' SEQ ID NO:7
5'GCA AGC AAT GAA GGT AC3' SEQ ID NO:8
These allele specific oligonucleotides are useful in diagnosis of a subject at risk of having breast or ovarian cancer. The allele specific oligonucleotides hybridize with a target polynucleotide sequence containing the 3772delTT mutation. 5'GCA AGC AAT TTG AAG GT3', SEQ ID NO:7, hybridizes preferentially to the wildtype sequence and is useful as a control sequence. 5'GCA AGC AAT GAA GGT AC3', SEQ ID NO:8, is designed to hybridize preferentially to the mutant sequence.

In a third embodiment of the invention a pair of isolated oligonucleotide primers are provided.
BRCA2-11F 5'GCA AAG ACC CTA AAG TAC AG3', SEQ ID NO:9
BRCA2-11R 5'CAT CAA ATA TTC CTT CTC TAA G3', SEQ ID NO:10
The oligonucleotide primers are useful in directing amplification of a target polynucleotide prior to sequencing. These unique BRCA2 exon 11 oligonucleotide primers were used to scan the BRCA2 gene to find the mutations. From the sequence information, the probes were designed and produced to assay for the mutation based upon identification of the C5193G mutation.

In another embodiment of the invention a pair of isolated allele specific oligonucleotides are provided.
5'ACT TGT TAC ACA AAT CA3', SEQ ID NO:11
5'ACT TGT TAG ACA AAT CA3', SEQ ID NO:12
These allele specific oligonucleotides are useful in diagnosis of a subject at risk of having breast or ovarian cancer. The allele specific oligonucleotides hybridize with a target polynucleotide sequence containing the C5193G mutation. 5'ACT TGT TAC ACA AAT CA3', SEQ ID NO:11, hybridizes preferentially to the wildtype sequence and is useful as a control sequence. 5'ACT TGT TAG ACA AAT CA3', SEQ ID NO:12, is designed to hybridize preferentially to the mutant sequence.

In a fourth embodiment of the invention a pair of isolated oligonucleotide primers are provided.
BRCA2-11F 5'GAA AAT TCA GCC TTA GC3' SEQ ID NO:13
BRCA2-11R 5'ATC AGA ATG GTA GGA AT3' SEQ ID NO:14

The oligonucleotide primers are useful in directing amplification of a target polynucleotide prior to sequencing. These unique BRCA2 exon 11 oligonucleotide primers were used to scan the BRCA2 gene to find the mutations. From the sequence information, the probes were designed and produced to assay for the mutation based upon identification of the 5374del4 mutation.

In another embodiment of the invention a pair of isolated allele specific oligonucleotides are provided.
5'ATT ATT TGT ATG AAA AT3' SEQ ID NO:15
5'ATT ATT TGA AAA TAA TT3' SEQ ID NO:16

These allele specific oligonucleotides are useful in diagnosis of a subject at risk of having breast or ovarian cancer. The allele specific oligonucleotides hybridize with a target polynucleotide sequence containing the 5374del4 mutation. 5'ATT ATT TGT ATG AAA AT3', SEQ ID NO:15, hybridizes preferentially to the wildtype sequence and is useful as a control sequence. 5'ATT ATT TGA AAA TAA TT3', SEQ ID NO:16, is designed to hybridize preferentially to the mutant sequence.

In a fifth embodiment of the invention a pair of isolated oligonucleotide primers are provided.
BRCA2-11F 5'TAC AGC AAG TGG AAA GC3' SEQ ID NO:17
BRCA2-11R 5'AAG TTT CAG TTT TAC CAA T3' SEQ ID NO:18

The oligonucleotide primers are useful in directing amplification of a target polynucleotide prior to sequencing. These unique BRCA2 exon 11 oligonucleotide primers were used to scan the BRCA2 gene to find the mutations. From the sequence information, the probes were designed and produced to assay for the mutation based upon identification of the 6495delGC mutation.

In another embodiment of the invention a pair of isolated allele specific oligonucleotides are provided.
5'GAA CTG AGC ATA GTC TT3' SEQ ID NO:19
5'GAA CTG AAT AGT CTT CA3' SEQ ID NO:20

These allele specific oligonucleotides are useful in diagnosis of a subject at risk of having breast or ovarian cancer. The allele specific oligonucleotides hybridize with a target polynucleotide sequence containing the 6495delGC mutation. 5'GAA CTG AGC ATA GTC TT3', SEQ ID NO:19, hybridizes preferentially to the wildtype sequence and is useful as a control sequence. 5'GAA CTG AAT AGT CTT CA3', SEQ ID NO:20, is designed to hybridize preferentially to the mutant sequence.

In a sixth embodiment of the invention a pair of isolated oligonucleotide primers are provided.
BRCA2-11F 5'ACT TTT TCT GAT GTT CCT GTG3' SEQ ID NO:21
BRCA2-11R 5'TAA AAA TAG TGA TTG GCA ACA3' SEQ ID NO:22

The oligonucleotide primers are useful in directing amplification of a target polynucleotide prior to sequencing. These unique BRCA2 exon 11 oligonucleotide primers were used to scan the BRCA2 gene to find the mutations. From the sequence information, the probes were designed and produced to assay for the mutation based upon identification of the 6909insG mutation.

In another embodiment of the invention a pair of isolated allele specific oligonucleotides are provided.
5'CAG AAG CAG TAG AAA TT3' SEQ ID NO:23
5'CAG AAG CAG GTA GAA AT3' SEQ ID NO:24

These allele specific oligonucleotides are useful in diagnosis of a subject at risk of having breast or ovarian cancer. The allele specific oligonucleotides hybridize with a target polynucleotide sequence containing the 6909insG mutation. 5'CAG AAG CAG TAG AAA TT3', SEQ ID NO:23, hybridizes preferentially to the wildtype sequence and is useful as a control sequence. 5'CAG AAG CAG GTA GAA AT3', SEQ ID NO:24, is designed to hybridize preferentially to the mutant sequence.

The primers of the invention embrace oligonucleotides of sufficient length and appropriate sequence to provide initiation of polymerization on a significant number of nucleic acids in the polymorphic locus.

Preferred sequences for the present invention are SEQ ID NO:1, SEQ ID NO:2, SEQ ID NO:5, SEQ ID NO:6, SEQ ID NO:9, SEQ ID NO:10, SEQ ID NO:13, SEQ ID NO:14, SEQ ID NO:17, SEQ ID NO:18, SEQ ID NO:21, and SEQ ID NO:22. Environmental conditions conducive to synthesis of extension products include the presence of nucleoside triphosphates, an agent for polymerization, such as DNA polymerase, and suitable conditions such as temperature, ionic strength and pH. The primer is preferably single stranded for maximum efficiency in amplification, but may be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the mutation to hybridize therewith and permit amplification of the genomic locus.

Oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al., *Tetrahedron Letters*, 22:1859–1862, (1981). One method for synthesizing oligonucleotides on a modified solid support is described in U.S. Pat. No. 4,458,066.

Any nucleic acid specimen, in purified or nonpurified form, can be utilized as the starting nucleic acid or acids, providing it contains, or is suspected of containing, the specific nucleic acid sequence containing the polymorphic locus. Thus, the process may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from a body sample, such as blood, tissue material and the like by a variety of techniques such as that described by Maniatis, et. al. in *Molecular Cloning:A Laboratory Manual*, Cold Spring Harbor, N.Y., p 280–281, 1982). If the extracted sample is impure, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. This is sufficient to denature any double strands. After this heating period, the solution is allowed to cool at a rate which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Thermostable DNA polymerases, such as Taq polymerase may function at a higher temperature.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. The suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. PCR. A Practical Approach, ILR Press, Eds. M. J. McPherson, P. Quirke, and G. R. Taylor, 1992.

The amplification products may be detected by analyzing it by Southern blots without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation. In the preferred embodiment, the amplification products are determinable by separating the mixture on an agarose gel containing ethidium bromide which causes DNA to be fluorescent.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et.al., *Bio/Technology*, 3:1008–1012, 1985), allele-specific oligonucleotide (ASO) probe analysis (Conner, et. al., *Proc. Natl. Acad. Sci. U.S.A.*, 80:278, 1983), oligonucleotide ligation assays (OLAs) (Landgren, et. al., *Science*, 241:1007, 1988), and the like. Molecular techniques for DNA analysis have been reviewed (Landgren, et. al., *Science*, 242:229–237, 1988).

Preferably, the method of amplifying is by PCR, as described herein and as is commonly used by those of ordinary skill in the art. Alternative methods of amplification have been described and can also be employed as long as the BRCA2 locus amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter olignucleotide and within a few hours, amplification is $10^8$ to $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking normal DNA repair. Nucleic acid amplification by strand displacement activation (SDA) utilizes a short primer containing a recognition site for Hinc II with short overhang on the 5' end which binds to target DNA. A DNA polymerase fills in the part of the primer opposite the overhang with sulfur-containing adenine analogs. Hinc II is added but only cuts the unmodified DNA strand. A DNA polymerase that lacks 5' exonuclease activity enters at the cite of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented Temperature cycling. Another amplification system useful in the method of the invention is the QB Replicase System. Although PCR is the preferred method of amplification in the invention, these other methods can also be used to amplify the BRCA2 locus as described in the method of the invention.

In another embodiment of the invention, a method is provided for diagnosing a subject having a predisposition or higher susceptibility to (at risk of) breast or ovarian cancer comprising sequencing a target nucleic acid of a sample from a subject by dideoxy sequencing following amplification of the target nucleic acid. In such an embodiment, one does not even need to use any of the oligonucleotides, either primers or probes, described herein. The BRCA2 gene, or fragments thereof, may be directly cloned and then sequenced (such as by dideoxy methods) to determine the presence or absence of a mutation. In such a situation, one need only compare the sequence obtained to a naturally occurring (wild type) BRCA2 gene, or portion thereof.

Other methods of DNA sequencing such as those of Sanger et al, *Proc. Natl. Acad. Sci. USA,* 74: 5463 (1977) or Maxam et al, *Proc. Natl. Acad. Sci. USA,* 74: 560 (1977) or other methods known in the art may be used.

In another embodiment of the invention a method is provided for diagnosing a subject having a predisposition or higher susceptibility to (at risk of) breast or ovarian cancer comprising contacting a target nucleic acid of a sample from a subject with a reagent that detects the presence of one of the mutations of the present invention and detecting the mutation.

In another embodiment of the invention, a method and reagents are provided for repairing the gene mutation in at least some cells by applying an oligomer comprising the sequence of the wild-type probes to repair the individual's genome by triple strand hybridization. See U.S. Pat. Nos. 5,650,316 and 5,624,803 for example. This is a form of gene therapy to correct the defect in either apparently normal tissue or in an active tumor. Gene repair may also be performed on excized tumor cells which may be helpful in determining the preferred therapy to be used, particularly the reagents used for gene therapy. Other forms of gene therapy, such as providing a complete copy of a normal BRCA2 gene may also be used.

In another embodiment of the invention a method is provided for characterizing a tumor. Histologic type, morphologic grade, differences between inherited and sporadic breast cancer do not appear to be distinguished. One method comprises sequencing the target nucleic acid isolated from the tumor or other biological sample to determine if the mutation is has occured or is present. Sanger, F., et al., *J. Mol. Biol.,* 142:1617 (1980).

Characterizing a tumor as having originated from an inherited breast cancer gene may be clinically significant as the prevalence of bilateral breast cancer is higher than in sproadic cases. Weber, *Scientific American,* January–February p. 12–21 (1996). The tumor may be classified based on tissue taken from the tumor itself or from a non-tumor site which contains genomic DNA.

Yet another embodiment of the present invention is an isolated mutant BRCA2 DNA sequence which may be the entire sequence, an exon thereof or a fragment thereof. The DNA sequence must contain at least one mutation from the list: C2192G, 3772delTT, C5193G, 5374del4, 6495delGC or 6909insG. Preferably, the isolated DNA sequence contains a sequence complementary to at least one of the following: SEQ ID NO:4, SEQ ID NO:8, SEQ ID NO:12:, SEQ ID NO:16, SEQ ID NO:20, or SEQ ID NO:24. This sequence has usefulness alone, or after cloning and expression to determine suitable treatments to prevent formation of a tumor, prevent transmission of the mutant gene to offspring or to decide other prophylactic diagnostic and treatment protocols. The isolated DNA sequence may also be used for drug design by protein replacement, protein mimetics, screening known and unknown compounds, anti-idiotype antibodies to the BRCA1 active site for the preparation of an immunogen or vaccine and determining appropriate gene therapy to counter the pathology associated with the mutant BRCA2 gene. For diagnostic purposes, knowing the mutant BRCA2 sequence for comparison purposes is the critical step in diagnosis.

Another method comprises contacting a target nucleic acid of a sample from a subject with a reagent that detects the presence of the mutation and detecting the mutation. A number of hybridization methods are well known to those skilled in the art. Many of them are useful in carrying out the invention.

The materials for use in the method of the invention are ideally suited for the preparation of a diagnostic kit. Such a kit may comprise a carrier means being compartmentalized to receive in close confinement one or more container means such as vials, tubes, and the like, each of the container means comprising one or more of the separate elements to be used in the method. For example, one of the container means may comprise means for amplifying BRCA2 DNA, said means comprising the necessary enzyme(s) and oligonucleotide primers for amplifying said target DNA from the subject. Another container may contain oligonucleotide probes for detecting the presence or absence of a mutation.

The oligonucleotide primers include primers having a sequence of SEQ ID NO:1, SEQ ID NO:2, SEQ ID NO:5, SEQ ID NO:6, SEQ ID NO:9, SEQ ID NO:10, SEQ ID NO:13, SEQ ID NO:14, SEQ ID NO:17, SEQ ID NO:18, SEQ ID NO:21, SEQ ID NO:22 or primer sequences substantially complementary or substantially homologous thereto. Other primers flanking the BRCA2 locus or a region containing one of the mutation sites may be used. The target flanking 5' and 3' polynucleotide sequence include other oligonucleotide primers for amplifying the BRCA2 locus will be known or readily ascertainable to those of skill in the art.

Oligonucleotide probes including probes having substantially the sequence of SEQ ID NO:3, SEQ ID NO:4, SEQ ID NO:7, SEQ ID NO:8, SEQ ID NO:11, SEQ ID NO:12, SEQ ID NO:15, SEQ ID NO:16, SEQ ID NO:19, SEQ ID NO:20, SEQ ID NO:23, SEQ ID NO:24. Other oligonucleotide probes which hybridize to one or more of the BRCA2 mutation sites and sequences substantially complementary or homologous thereto may be used. Other oligonucleotide probes for detecting the mutations will be known or readily ascertainable to those of skill in the art.

The following definitions are provided for the purpose of understanding this invention.

The term "primer" as used herein refers to a sequence comprising two or more deoxyribonucleotides or ribonucleotides, preferably more than three, and more preferably more than eight and most preferably at least 20 nucleotides of the BRCA2 gene wherein the sequence corresponds to a sequence flanking one of the mutations or wild type sequences of BRCA2 corresponding to the mutation sites. Primers may be used to initiate DNA synthesis via the PCR. The primers of the present invention include the sequences recited and complementary sequences which would aneal to the opposite DNA strand of the sample target. Since both strands of DNA are complementary and mirror images of each other, the same segment of DNA will be amplified.

The term "substantially complementary to" or "substantially the sequence" refers to sequences which hybridize to the sequences provided under stringent conditions and/or sequences having sufficient homology with, (e.g. SEQ ID NO:3 and SEQ ID NO:4) such that the allele specific oligonucleotides of the invention hybridize to the sequence. "Substantially" the same as it refers to oligonucleotide sequences also refers to the functional ability to hybridize or aneal with sufficient specificity to distinguish between the presence or absence of the mutation. This is measurable by the temperature of melting being sufficiently different to permit easy identification of whether the oligonucleotide is binding to the normal or mutant BRCA2 gene sequence.

The term "isolated" as used herein refers to being substantially free of other polynucleic acids, proteins, lipids, carbohydrates or other materials with which they may be associated. Such association being either in cellular material or in a synthesis medium.

"Biological sample" refers to a polynucleotide containing sample originally from a biological source. The sample may be from a living, dead or even archeological source from a variety of tissues and cells. Examples include: body fluid [blood (leukocytes), urine (epithelial cells), saliva, cervical and vaginal secretions . . . ] skin, hair roots/follicle, mucus membrane (e.g. buccal or tongue cell scrapings), cervico-vaginal cells (from PAP smear, etc.) internal tissue (normal or tumor), chorionic villus tissue, amnionic cells, placental cells, fetal cells, cord blood, sperm or egg.

"Coding sequence" or "DNA coding sequence" refers to those portions of a gene which, taken together, code for a peptide (protein), or for which the nucleic acid itself has function.

A "target polynucleotide" refers to the nucleic acid sequence of interest e.g., the BRCA2 encoding polynucleotide.

"Consensus" means the most commonly occurring in the population.

"Cancer", "tumor" and other similar terms refer to any neoplasm whether benign or malignant, and regardless of whether it has metastisized or the location of the "cancer" or "tumor".

"Substantially complementary to" refers to probe or primer sequences which hybridize to the sequences listed under stringent conditions and/or sequences having sufficient homology with test polynucleotide sequences, such that the allele specific oligonucleotide probe or primers hybridize to the test polynucleotide sequences to which they are complimentary.

"Sequence variation" as used herein refers to any difference in nucleotide sequence between two different oligonucleotide or polynucleotide sequences.

"Polymorphism" as used herein refers to a sequence variation in a gene which is not necessarily associated with pathology.

"Mutation" as used herein refers to an altered genetic sequence which results in the gene coding for a non-functioning protein or a protein with substantially reduced or altered function. Generally, a deleterious mutation is associated with pathology or the potential for pathology.

"Pre-determined sequence variation" as used herein refers to a nucleotide sequence that is designed to be different than the corresponding sequence in a reference nucleotide sequence. A pre-determined sequence variation can be a known mutation in the BRCA2 gene.

"BRCA2 gene" is a group of compounds and refers to the published gene sequences, those appearing in the GEN-BANK database and the BIC database. Other different sequences include polymorphisms and genetic alterations, especially those which define other haplotypes for the BRCA2 gene. Generally polymorphisms which don't cause an amino acid change or which are naturally occurring (wild types), which are not associated with pathology are also considered the BRCA2 gene. The corresponding nucleotides would then be used even if the nucleotide number differs. While the BRCA2 gene discussed herein is the human BRCA2 gene, the corresponding assays and reagents for the gene in other animals may also be used. The BRCA2 gene includes the coding sequences, non-coding sequences (e.g. introns) and regulatory regions affecting gene expression.

"Allele specific detection assay" as used herein refers to an assay to detect the presence or absence of a predetermined sequence variation in a test polynucleotide or oligonucleotide by annealing the test polynucleotide or oligonucleotide with a polynucleotide or oligonucleotide of predetermined sequence such that differential DNA sequence based techniques or DNA amplification methods discriminate between normal and mutant.

"Sequence variation locating assay" as used herein refers to an assay that detects a sequence variation in a test polynucleotide or oligonucleotide and localizes the position of the sequence variation to a subregion of the test polynucleotide, without necessarily determining the precise base change or position of the sequence variation.

"Region" as used herein generally refers to an area from several nucleotides upstream to several nucleotides downstream from the specific nucleotide mentioned. "Region" also includes the complementary nucleotides on the antisense strand of sample DNA.

"Targeted confirmatory sequencing" as used herein refers to sequencing a polynucleotide in the region wherein a sequence variation has been located by a sequence variation locating assay in order to determine the precise base change and/or position of the sequence variation.

"Probe" includes any oligonucleotide which hybridizes to a BRCA2 or mutant BRCA2 sequence. The probe may be labeled (directly or indirectly) or it may act as a primer such as a PCR primer. The probes of the present invention include the sequences recited and complementary sequences which would aneal to the antisense strand of the sample target DNA. Since both strands of DNA are complementary and mirror images of each other, the complementary version of the mutation is equally unique and indicative of the mutation to be assayed.

Allele Specific Oligonucleotide hybridization is sometimes referred to ASO or the ASO method.

The invention in several of its embodiments includes:

Detection Of Pre-Determined Sequence Variations

Stage I analysis may be used to determine the presence or absence of a pre-determined nucleotide sequence variation; preferably a known mutation or set of known mutations in the test gene. In accordance with the invention, such pre-determined sequence variations are detected by allele specific hybridization, a sequence-dependent-based technique which permits discrimination between normal and mutant alleles. An allele specific assay is dependent on the differential ability of mismatched nucleotide sequences (e.g., normal:mutant) to hybridize with each other, as compared with matching (e.g., normal:normal or mutant:mutant) sequences.

Detection Of Pre-Determined Sequence Variations Using Allele Specific Hydridization A variety of methods well-known in the art can be used for detection of pre-determined sequence variations by allele specific hybridization. Preferably, the test gene is probed with allele specific oligonucleotides (ASOs); and each ASO contains the sequence of a known mutation. ASO analysis detects specific sequence variations in a target polynucleotide fragment by testing the ability of a specific oligonucleotide probe to hybridize to the target polynucleotide fragment. Preferably, the oligonucleotide contains the mutant sequence (or its complement). The presence of a sequence variation in the target sequence is indicated by hybridization between the oligonucleotide probe and the target fragment under conditions in which an oligonucleotide probe containing a normal sequence does not hybridize to the target fragment. A lack of hybridization between the sequence variant (e.g., mutant) oligonucleotide probe and the target polynucleotide fragment indicates the absence of the specific sequence variation (e.g., mutation) in the target fragment. In a preferred embodiment, the test samples are probed in a standard dot blot format. Each region within the test gene that contains the sequence corresponding to the ASO is individually applied to a solid surface, for example, as an individual dot on a membrane. Each individual region can be produced, for example, as a separate PCR amplification product using methods well-known in the art (see, for example, the experimental embodiment set forth in Mullis, K. B., 1987, U.S. Pat. No. 4,683,202). The use of such a dot blot format is described in detail in the Examples below, detailing the Stage I analysis of the human BRCA2 gene to detect the presence or absence of six different known mutations using six corresponding ASOs.

Membrane-based formats that can be used as alternatives to the dot blot format for performing ASO analysis include, but are not limited to, reverse dot blot, (multiplex amplification assay), and multiplex allele-specific diagnostic assay (MASDA).

In a reverse dot blot format, oligonucleotide or polynucleotide probes having known sequence are immobilized on the solid surface, and are subsequently hybridized with the labeled test polynucleotide sample. In this situation, the primers may be labeled or the NTPs maybe labeled prior to amplification to prepare a labeled test polynucleotide sample. Alternatively, the test polynucleotide sample may be labeled subsequent to isolation and/or synthesis.

In a multiplex format, individual samples contain multiple target sequences within the test gene, instead of just a single target sequence. For example, multiple PCR products each containing at least one of the ASO target sequences are applied within the same sample dot. Multiple PCR products can be produced simultaneously in a single amplification reaction using the methods of Caskey et al., U.S. Pat. No. 5,582,989. The same blot, therefore, can be probed by each ASO whose corresponding sequence is represented in the sample dots.

A MASDA format expands the level of complexity of the multiplex format by using multiple ASOs to probe each blot (containing dots with multiple target sequences). This procedure is described in detail in U.S. Pat. No. 5,589,330 by A. P. Shuber, and in Michalowsky et al., *American Journal of Human Genetics*, 59(4): A272, poster 1573, October 1996, each of which is incorporated herein by reference in its entirety. First, hybridization between the multiple ASO probe and immobilized sample is detected. This method relies on the prediction that the presence of a mutation among the multiple target sequences in a given dot is sufficiently rare that any positive hybridization signal results from a single ASO within the probe mixture hybridizing with the corresponding mutant target. The hybridizing ASO is then identified by isolating it from the site of hybridization and determining its nucleotide sequence.

Suitable materials that can be used in the dot blot, reverse dot blot, multiplex, and MASDA formats are well-known in the art and include, but are not limited to nylon and nitrocellulose membranes.

When the target sequences are produced by PCR amplification, the starting material can be chromosomal DNA in which case the DNA is directly amplified. Alternatively, the starting material can be mRNA, in which case the mRNA is first reversed transcribed into cDNA and then amplified according to the well known technique of RT-PCR (see, for example, U.S. Pat. No. 5,561,058 by Gelfand et al.).

The methods described above are suitable for moderate screening of a limited number of sequence variations. However, with the need in molecular diagnosis for rapid, cost effective large scale screening, technologies have developed that integrate the basic concept of ASO, but far exceed the capacity for mutation detection and sample number. These alternative methods to the ones described above include, but are not limited to, large scale chip array sequence-based techniques. The use of large scale arrays allows for the rapid analysis of many sequence variants. A review of the differences in the application and development of chip arrays is covered by Southern, E. M., *Trends In Genetics*, 12: 110–115 (March 1996) and Cheng et al., *Molecular Diagnosis*, 1:183–200 (September 1996). Several approaches exist involving the manufacture of chip arrays. Differences include, but not restricted to: type of solid support to attach the immobilized oligonucleotides, labeling techniques for identification of variants and changes in the sequence-based techniques of the target polynucleotide to the probe.

A promising methodology for large scale analysis on 'DNA chips' is described in detail in Hacia et al., *Nature Genetics*, 14:441–447, (1996) which is hereby incorporated by reference in its entirety. As described in Hacia et al., high density arrays of over 96,000 oligonucleotides, each 20 nucleotides in length, are immobilized to a single glass or silicon chip using light directed chemical synthesis. Contingent on the number and design of the oligonucleotide probe, potentially every base in a sequence can be interrogated for alterations. Oligonucleotides applied to the chip, therefore, can contain sequence variations that are not yet known to occur in the population, or they can be limited to mutations that are known to occur in the population.

Prior to hybridization with olignucleotide probes on the chip, the test sample is isolated, amplified and labeled (e.g. fluorescent markers) by means well known to those skilled in the art. The test polynucleotide sample is then hybridized to the immobilized oligonucleotides. The intensity of sequence-based techniques of the target polynucleotide to the immobilized probe is quantitated and compared to a reference sequence. The resulting genetic information can be used in molecular diagnosis.

A common, but not limiting, utility of the 'DNA chip' in molecular diagnosis is screening for known mutations. However, this may impose a limitation on the technique by only looking at mutations that have been described in the field. The present invention allows allele specific hybridization analysis be performed with a far greater number of mutations than previously available. Thus, the efficiency and comprehensiveness of large scale ASO analysis will be broadened, reducing the need for cumbersome end-to-end sequence analysis, not only with known mutations but in a comprehensive manner all mutations which might occur as predicted by the principles accepted, and the cost and time associated with these cumbersome tests will be decreased.

EXAMPLE

Genomic DNA (at least 100 ng) is isolated from white blood cells of a subject with a family history of breast, ovarian or other cancer. Dideoxy sequence analysis is performed following polymerase chain reaction amplification of segments of exon 11.

Exon 11 of the BRCA2 gene is subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye is attached for automated sequencing using the TAQ DYE TERMINATOR KIT (PERKIN-ELMER cat# 401628). DNA sequencing is performed in both forward and reverse directions on an APPLIED BIOSYSTEMS, INC. (ABI) automated sequencer (Model 373 or 377). The software used for analysis of the resulting data is "SEQUENCE NAVIGATOR" purchased through ABI.

The methods of the invention, which can be used to detect sequence variations in any polynucleotide sample, are demonstrated in the Example set forth in this section, for the purpose of illustration, for one gene in particular, namely, the human BRCA2 gene. The BRCA2 coding sequence is approximately 10,248 base pairs encoding the 3418 amino acid BRCA2 protein.

Designing an Allele Specific Oligonucleotide (ASO) Probe

An allele specific oligonucleotide probe is a short, single stranded polynucleotide that is engineered to hybridize exactly to a target sequence under a given set of conditions. Routinely, ASO probes are designed to contain sequences identical to the normal allele and sequence variation respectively. Hybridization of the probe to the target allows for the discrimination of a variant sample. Under stringent conditions, a probe with a variation as simple as a single-base pair will not hybridize to a normal sequence due to a destabilizing effect of the normal-mutant duplex (Ikuta, S. et al, *Nucleic Acids Research*, 15: 797–811 (1987). For use in this invention, probes were used to discriminate between a wild-type or normal sequence from one that is mutated. Each probe pair contained a polynucleotide sequence that encompassed an area that would identify a selected mutation of the BRCA 2 gene.

The design of an ASO hybridization probe must meet two basic requirements. (*Current Protocols in Human Genetics*, section 9.4, (1995)). First, probes that are used together in the same pool should be around the same length. Although the standard length of a probe is optimally 17 base pairs, the range can be as short as about 14 or as long as about 24. Second, the mismatched region should not be placed at the end of the 17 base pair probe, but approximately in the middle of the sequence, approximately 5–7 bases from the 5' end of the probe. In addition, the placement of a mismatch, in the case of a longer probe, should not be at the end, but at a position that allows strong hybridization and stabilization of the polynucleotide strand. In order to minimize the effects of variations in base composition of the probes, tetramethylammonium chloride is used as in the ASO hybrid's buffer (Shuber, T., U.S. Pat. No. 5,633,134). Conventionally, ASO probes are synthesized on a DNA synthesizer. They can be labeled with isotopic or non-isotopic detection agents using means familiar to those of skill in the art. The process outlined in this application for making and using probes can be applicable for other gene sequences.

Detailed Method For The Detection Of Sequence Variations In Polynucleotides

Isolation of Genomic DNA

White blood cells were collected from the patient and genomic DNA is extracted from the white blood cells according to well-known methods (Sambrook, et al., Molecular Cloning, A Laboratory Manual, 2nd Ed., 1989, Cold Spring Harbor Laboratory Press, at 9.16–9.19).

PCR Amplification for Sequencing

The genomic DNA is used as a template to amplify a separate DNA fragment encompassing the site of the mutation to be tested. The 25 $\mu$l PCR reaction contained the following components: 1 $\mu$l template (100 ng/$\mu$l) DNA, 2.5 $\mu$l 10× PCR Buffer (PERKIN-ELMER), 1.5 $\mu$l dNTP (2 mM each DATP, dCTP, dGTP, dTTP), 1.5 $\mu$l Forward Primer (10 $\mu$M), 1.5 $\mu$l Reverse Primer (10 $\mu$M), 0.5 $\mu$l (2.5 U total) AMPLITAQ GOLD™ TAQ DNA POLYMERASE or AMPLITAQ® TAQ DNA POLYMERASE (PERKIN-ELMER), 1.0 to 5.0 $\mu$l (25 mM) $MgCl_2$ (depending on the primer) and distilled water ($dH_2O$) up to 25 $\mu$l. All reagents for each exon except the genomic DNA can be combined in a master mix and aliquoted into the reaction tubes as a pooled mixture.

For each exon analyzed, the following control PCRs were set up:
(1) "Negative" DNA control (100 ng placental DNA (SIGMA CHEMICAL CO., St. Louis, Mo.)
(2) Three "no template" controls PCR for all exons is performed using the following thermocycling conditions:

| Temperature | Time | Number of Cycles |
|---|---|---|
| 95° C. | 5 min. (AMPLITAQ) or 10 min. (GOLD) | 1 |
| 95° C. | 30 sec. | |
| 55° C. | 30 sec. | 30 cycles |
| 72° C. | 1 min | |
| 72° C. | 5 min. | 1 |
| 4° C. | infinity | 1 |

Quality Control Agarose Gel of PCR Amplification

The quality of the PCR products were examined prior to further analysis by electrophoresing an aliquot of each PCR reaction sample on an agarose gel. 5 $\mu$l of each PCR reaction is run on an agarose gel along side a DNA 100BP DNA LADDER (Gibco BRL cat# 15628-019). The electrophoresed PCR products were analyzed according to the following criteria:

Each patient sample must show a single band of the size corresponding the number of base pairs expected from the length of the PCR product from the forward primer to the reverse primer. If a patient sample demonstrates smearing or multiple bands, the PCR reaction must be repeated until a clean, single band is detected. If no PCR product is visible or if only a weak band is visible, but the control reactions with placental DNA template produced a robust band, the patient sample should be re-amplified with 2× as much template DNA.

All three "no template" reactions must show no amplification products. Any PCR product present in these reactions is the result of contamination. If any one of the "no template" reactions shows contamination, all PCR products should be discarded and the entire PCR set of reactions should be repeated after the appropriate PCR decontamination procedures have been taken.

The optimum amount of PCR product on the gel should be between 50 and 100 ng, which can be determined by comparing the intensity of the patient sample PCR products with that of the DNA ladder. If the patient sample PCR products contain less than 50 to 100 ng, the PCR reaction should be repeated until sufficient quantity is obtained.

DNA Sequencing

For DNA sequencing, double stranded PCR products are labeled with four different fluorescent dyes, one specific for each nucleotide, in a cycle sequencing reaction. With Dye Terminator Chemistry, when one of these nucleotides is incorporated into the elongating sequence it causes a termination at that point. Over the course of the cycle sequencing reaction, the dye-labeled nucleotides are incorporated along the length of the PCR product generating many different length fragments.

The dye-labeled PCR products will separate according to size when electrophoresed through a polyacrylamide gel. At the lower portion of the gel on an ABI automated sequencers, the fragments pass through a region where a laser beam continuously scans across the gel. The laser excites the fluorescent dyes attached to the fragments causing the emission of light at a specific wavelength for each dye. Either a photomultiplier tube (PMT) detects the fluorescent light and converts is into an electrical signal (ABI 373) or the light is collected and separated according to wavelength by a spectrograph onto a cooled, charge coupled device (CCD) camera (ABI 377). In either case the data collection software will collect the signals and store them for subsequent sequence analysis.

PCR products were first purified for sequencing using a QIAQUICK-SPIN PCR PURIFICATION KIT (QIAGEN #28104). The purified PCR products were labeled by adding primers, fluorescently tagged dNTPs and Taq Polymerase FS in an ABI Prism Dye Terminator Cycle Sequencing Kit (PERKIN ELMER/ABI catalog #02154) in a PERKIN ELMER GENEAMP 9600 thermocycler.

The amounts of each component are:

| For Samples | | For Controls | |
| --- | --- | --- | --- |
| Reagent | Volume | Reagent | Volume |
| Dye mix | 8.0 µL | PGEM | 2.0 µL |
| Primer (1.6 mM) | 2.0 µL | M13 | 2.0 µL |
| PCR product | 2.0 µL | Dye mix | 8.0 µL |
| sdH2O | 8.0 µL | sdH2O | 8.0 µL |

The thermocycling conditions were:

| Temperature | Time | # of Cycles |
| --- | --- | --- |
| 96° C. | 15 sec. | |
| 50° C. | 5 sec. | 25 |
| 60° C. | 4 min. | |
| 4° C. | Infinity | 1 |

The product was then loaded into a gel and placed into an ABI DNA Sequencer (Models 373A & 377) and run. The sequence obtained was analyzed by comparison to the wild type (reference) sequence within the SEQUENCE NAVIGATOR. When a sequence does not align, it indicates a possible mutation. The DNA sequence was determined in both the forward and reverse direction. All results were provided to a second reader for review.

Heterozygous/homozygous point mutations and polymorphisms must be seen in both strands. Frameshift mutations will be seen in both strands and must have clear double peaks in frame shift regions to be so identified.

PCR Amplification for ASO

The genomic DNA is used as a template to amplify a separate DNA fragment encompassing the site of the mutation to be tested. The 50 µl PCR reaction contained the following components: 1 µl template (100 ng/µl) DNA, 5.0 µl 10× PCR Buffer (PERKIN-ELMER), 2.5 µl dNTP (2 mM each DATP, dCTP, dGTP, dTTP), 2.5 µl Forward Primer (10 µM), 2.5 µl Reverse Primer (10 µM), 0.5 µl (2.5 U total) AMPLITAQ® TAQ DNA POLYMERASE or AMPLITAQ GOLD™ DNA POLYMERASE (PERKIN-ELMER), 1.0 to 5.0 µl (25 mM) $MgCl_2$ (depending on the primer) and distilled water ($dH_2O$) up to 50 µl. All reagents for each exon except the genomic DNA can be combined in a master mix and aliquoted into the reaction tubes as a pooled mixture.

For each exon analyzed, the following control PCRs were set up:

(1) "Negative" DNA control (100 ng placental DNA (SIGMA CHEMICAL CO., St. Louis, Mo.)

(2) Three "no template" controls

PCR for all exons is performed using the following thermocycling conditions:

| Temperature | Time | Number of Cycles |
| --- | --- | --- |
| 95° C. | 5 min. (AMPLITAQ) or 10 min. (GOLD) | 1 |
| 95° C. | 30 sec. | |
| 55° C. | 30 sec. | 30 cycles |
| 72° C. | 1 min | |
| 72° C. | 5 min. | 1 |
| 4° C. | infinity | 1 |

The quality control agarose gel of PCR amplification was performed as above.

Binding PCR Products to Nylon Membrane

The PCR products are denatured no more than 30 minutes prior to binding the PCR products to the nylon membrane. To denature the PCR products, the remaining PCR reaction (45 µl) and the appropriate positive control mutant gene amplification product are diluted to 200 µl final volume with PCR Diluent Solution (500 mM NaOH, 2.0 M NaCl, 25 mM EDTA) and mixed thoroughly. The mixture is heated to 95° C. for 5 minutes, and immediately placed on ice and held on ice until loaded onto dot blotter, as described below.

The PCR products are bound to 9 cm by 13 cm nylon ZETA PROBE BLOTTING MEMBRANE (BIO-RAD, Hercules, Calif., catalog number 162-0153) using a BIO-RAD dot blotter apparatus. Forceps and gloves are used at all times throughout the ASO analysis to manipulate the membrane, with care taken never to touch the surface of the membrane with bare hands or latex gloves.

Pieces of 3 MM filter paper [WHATMAN®, Clifton, N.J.] and nylon membrane are pre-wet in 10× SSC prepared fresh from 20× SSC buffer stock. The vacuum apparatus is rinsed thoroughly with $dH_2O$ prior to assembly with the membrane. 100 µl of each denatured PCR product is added to the wells of the blotting apparatus. Each row of the blotting apparatus contains a set of reactions for a single exon to be tested, including a placental DNA (negative) control, a synthetic oligonucleotide with the desired mutation or a PCR product from a known mutant sample (positive control), and three no template DNA controls.

After applying PCR products, the nylon filter is placed DNA side up on a piece of 3 MM filter paper saturated with denaturing solution (1.5M NaCl, 0.5 M NaOH) for 5 minutes. The membrane is transferred to a piece of 3 MM filter paper saturated with neutralizing solution (1M Tris-HCl, pH 8, 1.5 M NaCl) for 5 minutes. The neutralized membrane is then transferred to a dry 3 MM filter DNA side up, and exposed to ultra-violet light (STRALINKER, STRATAGENE, La Jolla, Calif.) for exactly 45 seconds the fix the DNA to the membrane. This UW crosslinking should be performed within 30 min. of the denaturation/neutralization steps. The nylon membrane is then cut into strips such that each strip contains a single row of blots of one set of reactions for a single exon.

Hybridizing Labeled Oligonucleotides to the Nylon Membrane

Prehybridization

The strip is prehybridized at 52° C. using the HYBAID® (SAVANT INSTRUMENTS, INC., Holbrook, N.Y.) hybridization oven. 2× SSC (15 to 20 ml) is preheated to 52° C. in a water bath. For each nylon strip, a single piece of nylon mesh cut slightly larger than the nylon membrane strip (approximately 1"×5") is pre-wet with 2× SSC. Each single nylon membrane is removed from the prehybridization solution and placed on top of the nylon mesh. The membrane/mesh "sandwich" is then transferred onto a piece of Parafilm. The membrane/mesh sandwich is rolled lengthwise and placed into an appropriate HYBAID® bottle, such that the rotary action of the HYBAID® apparatus caused the membrane to unroll. The bottle is capped and gently rolled to cause the membrane/mesh to unroll and to evenly distribute the 2× SSC, making sure that no air bubbles formed between the membrane and mesh or between the mesh and the side of the bottle. The 2× SSC is discarded and replaced with 5 ml TMAC Hybridization Solution, which contained 3 M TMAC (tetramethyl ammoniumchloride—SIGMA T-3411), 100 mM $Na_3PO_4$(pH6.8), 1 mM EDTA, 5× Denhardt's (1% Ficoll, 1% polyvinylpyrrolidone, 1% BSA (fraction V)), 0.6% SDS, and 100 µg/ml Herring Sperm DNA. The filter strips were prehybridized at 52° C. with medium rotation (approx. 8.5 setting on the HYBAID® speed control) for at least one hour. Prehybridization can also be performed overnight.

Labeling Oligonucleotides

The DNA sequences of the oligonucleotide probes used to detect the BRCA2 mutations are as follows (for each mutation, a mutant and a normal oligonucleotide must be labeled):

C2192G—normal 5'TGA AGA ACC AAC TTT GT3' SEQ ID NO:3
C2192G—mutant 5'TGA AGA ACG AAC TTT GT3' SEQ ID NO:4
3772delTT—normal 5'GCA AGC AAT TTG AAG GT3' SEQ ID NO:7
3772delTT—mutant 5'GCA AGC AAT GAA GGT AC3' SEQ ID NO:8
C5193G—normal 5'ACT TGT TAC ACA AAT CA3'SEQ ID NO:11
C5193G—mutant 5'ACT TGT TAG ACA AAT CA3' SEQ ID NO:12
5374del4—normal 5'ATT ATT TGT ATG AAA AT3' SEQ ID NO:15
5374del4—mutant 5'ATT ATT TGA AAA TAA TT3' SEQ ID NO:16
6495delGC—normal 5'GAA CTG AGC ATA GTC TT3' SEQ ID NO:19
6495delGC—mutant 5'GAA CTG AAT AGT CTT CA3' SEQ ID NO:20
6909insG—normal 5'CAG AAG CAG TAG AAA TT3' SEQ ID NO:23
6909insG—mutant 5'CAG AAG CAG GTA GAA AT3' SEQ ID NO:24

Each labeling reaction contains 2-µl 5× Kinase buffer (or 1 µl of 10× Kinase buffer), 5 µl gamma-ATP $^{32}P$ (not more than one week old), 1 µl T4 polynucleotide kinase, 3 µl oligonucleotide (20 µM stock), sterile $H_2O$ to 10 µl final volume if necessary. The reactions are incubated at 37° C. for 30 minutes, then at 65° C. for 10 minutes to heat inactivate the kinase. The kinase reaction is diluted with an equal volume (10 µl) of sterile $dH_2O$ (distilled water).

The oligonucleotides are purified on STE MICRO SELECT-D, G-25 spin columns (catalog no. 5303-356769), according to the manufacturer's instructions. The 20 µl synthetic oligonucleotide eluate is diluted with 80 µl $dH_2O$ (final volume=100 µl). The amount of radioactivity in the oligonucleotide sample is determined by measuring the radioactive counts per minute (cpm). The total radioactivity must be at least 2 million cpm. For any samples containing less than 2 million total, the labeling reaction is repeated.

Hybridization with Mutant Oligonucleotides

Approximately 2–5 million counts of the labeled mutant oligonucleotide probe is diluted into 5 ml of TMAC hybridization solution, containing 40 µl of 20 µM stock of unlabeled normal oligonucleotide. The probe mix is preheated to 52° C. in the hybridization oven. The pre-hybridization solution is removed from each bottle and replaced with the probe mix. The filter is hybridized for 1 hour at 52° C. with moderate agitation. Following hybridization, the probe mix is decanted into a storage tube and stored at −20° C. The filter is rinsed by adding approximately 20 ml of 2× SSC+0.1% SDS at room temperature and rolling the capped bottle gently for approximately 30 seconds and pouring off the rinse. The filter is then washed with 2× SSC+0.1% SDS at room temperature for 20 to 30 minutes, with shaking.

The membrane is removed from the wash and placed on a dry piece of 3 MM WHATMAN filter paper then wrapped in one layer of plastic wrap, placed on the autoradiography film, and exposed for about five hours depending upon a survey meter indicating the level of radioactivity. The film is developed in an automatic film processor.

Control Hybridization with Normal Oligonucleotides

The purpose of this step is to ensure that the PCR products are transferred efficiently to the nylon membrane.

Following hybridization with the mutant oligonucleotide, as described in the Examples above, each nylon membrane is washed in 2× SSC, 0.1% SDS for 20 minutes at 65° C. to melt off the mutant oligonucleotide probes. The nylon strips were then prehybridized together in 40 ml of TMAC hybridization solution for at least 1 hour at 52° C. in a shaking water bath. 2–5 million counts of each of the normal labeled oligonucleotide probes plus 40 µl of 20 µM stock of unlabeled normal oligonucleotide are added directly to the container containing the nylon membranes and the prehybridization solution. The filter and probes are hybridized at 52° C. with shaking for at least 1 hour. Hybridization can be performed overnight, if necessary. The hybridization solution is poured off, and the nylon membrane is rinsed in 2× SSC, 0.1% SDS for 1 minute with gentle swirling by hand.

The rinse is poured off and the membrane is washed in 2× SSC, 0.1% SDS at room temperature for 20 minutes with shaking.

The nylon membrane is removed and placed on a dry piece of 3 MM WHATMAN filter paper. The nylon membrane is then wrapped in one layer of plastic wrap and placed on autoradiography film, and exposure is for at least 1 hour.

For each sample, adequate transfer to the membrane is indicated by a strong autoradiographic hybridization signal. For each sample, an absent or weak signal when hybridized with its normal oligonucleotide, indicates an unsuccessful transfer of PCR product, and it is a false negative. The ASO analysis must be repeated for any sample that did not successfully transfer to the nylon membrane.

Interpreting Results

After hybridizing with mutant oligonucleotides, the results for each exon are interpreted as follows:

The sample #1 should be lighter than the controls. Patient samples containing a mutation are generally heterozygous and will hybridize to both the normal and mutant oligonucleotide probes. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

All references mentioned herein are incorporated by reference.

TABLE 4A

| Result | Interpretation | Action |
|---|---|---|
| ● ○  ○ ○ ○<br>(+) (-)  NT NT NT | All controls indicate assay is successful | Record results, dark circles are mutation positive, and all others are negative |
| ● ●  ○ ○ ○<br>(+) (-)  NT NT NT | Assay not specific, mutant oligonucleotide hybridizing to normal DNA. | Rewash membrane 30 minutes longer at appropriate temp. and re-expose. |
| ○ ○  ○ ○ ○<br>(+) (-)  NT NT NT | Mutant oligonucleotide probe is either washed off or did not label well enough, or PCR product is not transferred to membrane efficiently. | Rehybridize with remaining labeled oligonucleotide. If still no signal, perform normal oligonucleotide hyb. as per the Examples to test transfer of PCR to membrane. |
| ● ○  ▨ ▨ ▨<br>(+) (-)  NT NT NT | Positive and negative controls indicate assay is successful, but PCR is contaminated. | Perform standard clean up procedures for PCR contamination. Repeat assay. |

After hybridization with normal oligonucleotides, interpret the results as follows:

TABLE 4B

| | | |
|---|---|---|
| ● ●  ○ ○ ○<br>(+) (-)  NT NT NT | Results indicate transfer of PCR products to membrane is successful. | Record results. |
| ● ●  ● ○ ○ ○<br>(+) (-)  #1 NT NT NT | Results indicate transfer of patient sample #1 is inefficient. May get false negative from this sample. | This sample will have to be transferred to another membrane and the assay repeated. |

We claim:

1. An isolated oligonucleotide wherein the oligonucleotide is capable of detecting a G at nucleotide number 2192 of a BRCA2 gene by specifically hybridizing to the region containing nucleotide number 2192 of the BRCA2 gene.

2. An isolated oligonucleotide having the sequence 5'TGA AGA ACC AAC TTT GT3', SEQ ID NO:3, or the complementary oligonucleotide thereto.

3. An isolated oligonucleotide according to claim 1 having the sequence 5'TGA AGA ACG AAC TTT GT3', SEQ ID NO:4, or the complementary oligonucleotide thereto.

4. The isolated oligonucleotide wherein the oligonucleotide is capable of detecting a deletion of TT at nucleotide number 3772 of a BRCA2 gene by specifically hybridizing to the region containing nucleotide number 3772 of the BRCA2 gene.

5. An isolated oligonucleotide having the sequence 5'GCA AGC AAT TTG AAG GT3', SEQ ID NO:7, or the complementary oligonucleotide thereto.

6. An isolated oligonucleotide according to claim 4 having the sequence 5'GCA AGC AAT GAA GGT AC3', SEQ ID NO:8, or the complementary oligonucleotide thereto.

7. An isolated oligonucleotide wherein the oligonucleotide is capable of detecting a substitution of G for C at nucleotide number 5193 of a BRCA2 gene by specifically hybridizing to the region containing nucleotide number 5193 of the BRCA2 gene.

8. An isolated oligonucleotide having the sequence 5'ACT TGT TAC ACA AAT CA3', SEQ ID NO:11, or the complementary oligonucleotide thereto.

9. An isolated oligonucleotide according to claim 7 having the sequence 5'ACT TGT TAG ACA AAT CA3', SEQ ID NO:12, or the complementary oligonucleotide thereto.

10. An isolated oligonucleotide according to claim 1 wherein the oligonucleotide is capable of detecting a deletion of TATG at nucleotide number 5374 of a BRCA2 gene by specifically hybridizing to the region containing nucleotide number 5374 of the BRCA2 gene.

11. An isolated oligonucleotide having the sequence 5'ATT ATT TGT ATG AAA AT3', SEQ ID NO:15, or the complementary oligonucleotide thereto.

12. An isolated oligonucleotide according to claim 10 having the sequence 5'ATT ATT TGA AAA TAA TT3', SEQ ID NO:16, or the complementary oligonucleotide thereto.

13. An isolated oligonucleotide wherein the oligonucleotide is capable of detecting a deletion of GC at nucleotide number 6495 of a BRCA2 gene by specifically hybridizing to the region containing nucleotide number 6495 of the BRCA2 gene.

14. An isolated oligonucleotide having the sequence 5'GAA CTG AGC ATA GTC TT3', SEQ ID NO:19, or the complementary oligonucleotide thereto.

15. An isolated oligonucleotide according to claim 13 having the sequence 5'GAA CTG AAT AGT CTT CA3', SEQ ID NO:20, or the complementary oligonucleotide thereto.

16. An isolated oligonucleotide wherein the oligonucleotide is capable of detecting an insertion of G at nucleotide number 6909 of a BRCA gene by specifically hybridizing to the region containing nucleotide number 6909 of the BRCA2 gene.

17. An isolated oligonucleotide having the sequence 5'CAG AAG CAG TAG AAA TT3', SEQ ID NO:23, or the complementary oligonucleotide thereto.

18. An isolated oligonucleotide according to claim 16 having the sequence 5'CAG AAG CAG GTA GAA AT3', SEQ ID NO:24, or the complementary oligonucleotide thereto.

19. The isolated oligonucleotide according to any one of claims 1, 4, 7, 10, 13 and 16 further comprising a label bound thereto.

20. The isolated oligonucleotide according to claim 19 wherein the label is selected from the group consisting of a radiolabel, a fluorescent label, a bioluminescent label, a chemiluminescent label, an enzyme label and a ligand label.

21. A pair of isolated oligonucleotide primers which specifically hybridize to the BRCA2 gene, said pair of primers selected from the group consisting of:
BRCA-2-11F: 5'TGG TAC TTT AAT TTT GTC ACT T3' (SEQ ID NO:1), and
BRCA-2-11R: 5'TGC AGG CAT GAC AGA GAA T3' (SEQ ID NO: 2);
BRCA-2-11F: 5'CTC AGA TGT TAT TTT CAA AGC3' (SEQ ID NO: 5); and
BRCA-2-11R: 5'CTG TTA AAT AAC CAG AAG CAC3' (SEQ ID NO: 6);
BRCA-2-11F: 5'GCA AAG ACC CTA AAG TAC AG3' (SEQ ID NO: 9), and
BRCA-2-11R: 5'CAT CAA ATA TTC CTT CTC TAA G3' (SEQ ID NO: 10);
BRCA-2-11F: 5'GAA AAT TCA GCC TTA GC3' (SEQ ID NO: 13), and
BRCA-2-11R: 5'ATC AGA ATG GTA GGA AT3' (SEQ ID NO: 14);
BRCA-2-11F: 5'TAC AGC AAG TGG AAA GC3' (SEQ ID NO: 17), and
BRCA-2-11R: 5'AAG TTT CAG TTT TAC CAA T3' (SEQ ID NO: 18); and
BRCA-2-11F: 5'ACT TTT TCT GAT GTT CCT GTG3' (SEQ ID NO: 21), and
BRCA-2-11R: 5'TAA AAA TAG TGA TTG GCA ACA3' (SEQ ID NO: 22).

22. The pair of isolated oligonucleotide primers according to claim 21, wherein each primer is bound to a label.

23. The pair of primers according to claim 22 wherein each of said label is selected from the group consisting of a radiolabel, a fluorescent label, a bioluminescent label, a chemiluminescent label, an enzyme label and a ligand label.

24. A method for determining the presence or absence of a sequence variation in the BRCA2 gene at nucleotide number 2192, 3772, 5193, 5374, 6495 or 6909 comprising:
(a) performing an allele specific detection assay for the presence or absence of one or more of said sequence variations; and
(b) determining the presence or absence of a sequence variation in the BRCA2 gene in the BRCA2 gene sample at nucleotide number 2192, 3772, 5193, 5374, 6495 or 6909.

25. The method according to claim 24 wherein the said sequence variation is C2192G, 3772delTT, C5193G, 5374del4, 6495delGC or 6909insG.

26. The method of claim 24 wherein the allele specific detection assay is performed as part of a multiplex amplification assay format.

27. The method of claim 24 wherein the allele specific detection assay is performed using a dot blot format, reverse dot blot format, a MASDA format, or a chip array format.

28. The method according to claim 24 further comprising
(a) performing an allele specific detection assay for the presence or absence of one or more reference sequences without said sequence variations.

29. The method according to claim 28 wherein said reference sequence is a BRCA2 coding sequence.

30. The method according to claim 28 wherein said reference sequence is a BRCA2 genomic sequence.

31. The method according to claim 28 wherein said reference sequence is one or more exons of the BRCA2 gene.

32. A method of detecting a predisposition or higher susceptibility to cancer in an individual, comprising:
(a) digesting DNA from an individual to obtain DNA fragments;
(b) separating said DNA fragments;
(c) detecting a DNA fragment containing nucleotide number 2192, 3772, 5193, 5374, 6495 or 6909 of the BRCA2 gene sequence or a sequence variation at nucleotide number 2192, 3772, 5193, 5374, 6495 or 6909 of the BRCA2 gene sequence by sequencing;
(d) comparing the sequence of said fragment with the BRCA2 gene sequence to determine the presence or absence of a sequence variation at nucleotide number 2192, 3772, 5193, 5374, 6495 or 6909, wherein the presence of a sequence variation indicates a predisposition or higher susceptibility to cancer.

33. A method according to claim 32 further comprising amplifying said DNA fragments prior to the detecting step (c).

34. A method according to claim 32 wherein the DNA fragment containing the sequence variation is amplified with an oligonucleotide primer having a sequence of:
5'TGG TAC TTT AAT TTT GTC ACT T3' SEQ ID NO:1,
5'TGC AGG CAT GAC AGA GAA T3' SEQ ID NO:2,
5'CTC AGA TGT TAT TTT CCA AGC3' SEQ ID NO:5,
5'CTG TTA AAT AAC CAG AAG CAC3' SEQ ID NO:6,
5'GCA AAG ACC CTA AAG TAC AG3' SEQ ID NO:9,
5'CAT CAA ATA TTC CTT CTC TAA G3' SEQ ID NO:10,
5'GAA AAT TCA GCC TTA GC3' SEQ ID NO:13,
5'ATC AGA ATG GTA GGA AT3' SEQ ID NO:14,
5'TAC AGC AAG TGG AAA GC3' SEQ ID NO:17,
5'AAG TTT CAG TTT TAC CAA T3' SEQ ID NO:18,
5'ACT TTT TCT GAT GTT CCT GTG3' SEQ ID NO:21,
5'TAA AAA TAG TGA TTG GCA ACA3' SEQ ID NO:22 or
a sequence capable of specific hybridization to and initiation of DNA synthesis on a complementary oligonucleotide or polynucleotide.

35. A method according to claim 34 wherein said oligonucleotide primer is labeled with a radiolabel, a fluorescent label a bioluminescent label, a chemiluminescent label, an enzyme label, or a ligand label.

36. A method of detecting a predisposition or higher susceptibility to cancer in an individual, comprising:
(a) digesting DNA from said individual to obtain DNA fragments,
(b) separating said DNA fragments obtained from said digestion,
(c) subjecting said DNA fragments to hybridization with an allele specific oligonucleotide having a nucleotide sequence capable of specifically hybridizing to a polynucleotide having a sequence variation at nucleotide number 2192, 3772, 5193, 5374, 6495 or 6909 of the BRCA2 gene sequence, thereby determining the absence or presence of said sequence variation in the BRCA2 gene of said individual, and
(d) correlating the presence of said sequence variation with a predisposition or higher susceptibility to cancer.

37. A method according to claim 36 herein said allele specific oligonucleotide is:
5'TGA AGA ACC AAC TTT GT3' SEQ ID NO:3,
5'TGA AGA ACG AAC TTT GT3' SEQ ID NO:4,
5'GCA AGC AAT TTG AAG GT3' SEQ ID NO:7,
5'GCA AGC AAT GAA GGT AC3' SEQ ID NO:8,
5'ACT TGT TAC ACA AAT CA3' SEQ ID NO:11,
5'ACT TGT TAG ACA AAT CA3' SEQ ID NO:12,
5'ATT ATT TGT ATG AAA AT3' SEQ ID NO:15,
5'ATT ATT TGA AAA TAA TT3' SEQ ID NO:16,
5'GAA CTG AGC ATA GTC TT3' SEQ ID NO:19,
5'GAA CTG AAT AGT CTT CA3' SEQ ID NO:20,
5'CAG AAG CAG TAG AAA TT3' SEQ ID NO:23, or
5'CAG AAG CAG GTA GAA AT3' SEQ ID NO:24.

38. A method according to claim 36 further comprising amplifying said DNA fragment prior to sequencing.

39. A method according to claim 36 wherein said oligonucleotide is labeled with a radiolabel, a fluorescent label, a bioluminescent label, a chemiluminescent label, an enzyme label, or a ligand label.

40. A kit comprising a carrier means being compartmentalized to receive in close confinement one or more container means, and at least one container means,
wherein said at least one container means contains the oligonucleotide of any one of claims 1, 4, 7, 10, 13, 16.

41. The kit according to claim 40 further comprising at least one container means containing:
BRCA-2-11F: 5'TGG TAC TTT AAT TTT GTC ACT T3' (SEQ ID NO:1),
BRCA-2 11R: 5'TGC AGG CAT GAC AGA GAA T3' (SEQ ID NO: 2),
BRCA-2-11F: 5'CTC AGA TGT TAT TTT CAA AGC3' (SEQ ID NO:5),
BRCA-2-11R: 5'CTG TTA AAT AAC CAG AAG CAC3' (SEQ ID NO: 6),
BRCA-2-11F: 5'GCA AAG ACC CTA AAG TAC AG3' (SEQ ID NO:9),
BRCA-2-11R: 5'CAT CAA ATA TTC CTT CTC TAA G3' (SEQ ID NO: 10),
BRCA-2-11F: 5'GAA AAT TCA GCC TTA GC3' (SEQ ID NO: 13),
BRCA-2-11R: 5'ATC AGA ATG GTA GGA AT3' (SEQ ID NO:14),
BRCA-2-11F: 5'TAC AGC AAG TGG AAA GC3' (SEQ ID NO: 17),
BRCA-2-11R: 5'AAG TTT CAG TTT TAC CAA T3' (SEQ ID NO:18),
BRCA-2-11F: 5'ACT TTT TCT GAT GTT CCT GTG3' (SEQ ID NO: 21), or
BRCA-2-11R: 5'TAA AAA TAG TGA TTG GCA ACA3' (SEQ ID NO: 22).

42. The kit according to claim 40 further comprising at least one container means containing a pair of isolated oligonucleotide primers which specifically hybridize to the BRCA2 gene, one of which can effectively hybridize to exon 11 of the BRCA2 gene, and the other can effectively hybridize to either exon 11 or one of the two intron regions flanking exon 11.

43. A kit comprising a carrier means being compartmentalized to receive in close confinement one or more container means, and at least one container means,
wherein at least one container means contains the pair of oligonucleotide primers of claim 21.

44. A method of determining whether a C2192G, 3772delTT, C5193G, 5374del4, 6495delGC, or 6909insG mutation is present in a BRCA2 gene comprising sequencing at least a portion of the BRCA2 gene containing either:
a sequence complementary to SEQ ID NO:4, SEQ ID NO:8, SEQ ID NO:12, SEQ ID NO:16:, SEQ ID NO:20 or SEQ ID NO:24, or an isolated DNA sequence while in the complement thereof, or
at least one mutation from the list: C2192G, 3772delTT, C5193G, 5374del4, 6495delGC or 6909insG.

* * * * *

UNITED STATES PATENT AND TRADEMARK OFFICE
CERTIFICATE OF CORRECTION

PATENT NO. : 6,051,379
DATED : April 18, 2000
INVENTOR(S) : Lescallett et al.

It is certified that error appears in the above-identified patent and that said Letters Patent is hereby corrected as shown below:

In the Claims:

Column 39, line 37: "according to claim 1" should be deleted;

Column 40, line 42: "6909" should read -- 6909, --;

Column 40, line 45: "variations; and" should read -- variations in the BRCA2 gene; and --;

Column 40, line 47: "in the BRCA2 gene" (second occurrence) should be deleted;

Column 40, line 50: "the" should be deleted;

Column 41, line 54: "sequence variation" should read --sequence contained within the BRCA2 gene sequence or a polynucleotide having a sequence variation--;

Column 41, line 61: "herein" should read -- wherein --;

Column 42, line 19: "containing:" should read -- containing an isolated nucleotide primer comprising the sequence: --;

Column 42, lines 56-57: "C2192G, 3772delTT, C5193G, 5374del4, 6495delGC, or 6909insG" should be deleted;

UNITED STATES PATENT AND TRADEMARK OFFICE
CERTIFICATE OF CORRECTION

PATENT NO. : 6,051,379
DATED : April 18, 2000
INVENTOR(S) : Lescallett et al.

It is certified that error appears in the above-identified patent and that said Letters Patent is hereby corrected as shown below:

Column 42, line 63: "while in" should read -- which is --;

Signed and Sealed this

Eighth Day of May, 2001

Attest:

NICHOLAS P. GODICI

Attesting Officer     Acting Director of the United States Patent and Trademark Office

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
       (A) ORGANISM: Homo sapiens
       (B) STRAIN: BRCA2

(xi) SEQUENCE DESCRIPTION: SEQ ID NO:1:

TGGTACTTTA ATTTTGTCAC TT                                            22

(2) INFORMATION FOR SEQ ID NO:2:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
       (A) ORGANISM: HOMO SAPIENS
       (B) STRAIN: BRCA2

(xi) SEQUENCE DESCRIPTION: SEQ ID NO:2:

TGCAGGCATG ACAGAGAA                                                 18

(2) INFORMATION FOR SEQ ID NO:3:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PROBE"

(iii) HYPOTHETICAL: NO (iv) ANTI-SENSE: YES (v) FRAGMENT TYPE: internal (vi) ORIGINAL SOURCE:
       (A) ORGANISM: HOMO SAPIENS (B) STRAIN: BRCA2

(xi) SEQUENCE DESCRIPTION: SEQ ID NO:3:

TGAAGAACCA ACTTTGT                                                    17

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:4:

TGAAGAACGA ACTTTGT                                                    17

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:5:

CTCAGATGTT ATTTTCCAAG C                                               21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:6:

CTGTTAAATA ACCAGAAGCA C                                                    21

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA2

(xi) SEQUENCE DESCRIPTION: SEQ ID NO:7:

GCAAGCAATT TGAAGGT                                                         17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA2

(xi) SEQUENCE DESCRIPTION: SEQ ID NO:8:

GCAAGCAATG AAGGTAC                                                         17

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA2

(xi) SEQUENCE DESCRIPTION: SEQ ID NO:9:

GCAAAGACCC TAAAGTACAG                    20

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:10:

CATCAAATAT TCCTTCTCTA AG                 22

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:11:

ACTTGTTACA CAAATCA                       17

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:12:

```
ACTTGTTAGA CAAATCA                                                          17

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:13:

GAAAATTCAG CCTTAGC                                                          17

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:14:

ATCAGAATGG TAGGAAT                                                          17

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:15:
```

```
ATTATTTGTA TGAAAAT                                                    17

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:16:

ATTATTTGAA AATAATT                                                    17

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:17:

TACAGCAAGT GGAAAGC                                                    17

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:18:

AAGTTTCAGT TTTACCAAT                                                  19
```

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:19:

GAACTGAGCA TAGTCTT                                                17

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:20:

GAACTGAATA GTCTTCA                                                17

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:21:

ACTTTTTCTG ATGTTCCTGT G                                           21

```
(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:22:

TAAAAATAGT GATTGGCAAC A                                              21

(2) INFORMATION FOR SEQ ID NO:23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:23:

CAGAAGCAGT AGAAATT                                                   17

(2) INFORMATION FOR SEQ ID NO:24:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA2

(xi) SEQUENCE DESCRIPTION: SEQ ID NO:24:

CAGAAGCAGG TAGAAAT                                                   17
```